(12) United States Patent
Krishnamoorthy (10) Patent No.: US 11,426,116 B2
(45) Date of Patent: Aug. 30, 2022

(54) SYSTEM USING EYE TRACKING DATA FOR ANALYSIS AND VALIDATION OF DATA (71) Applicant: BANK OF AMERICA CORPORATION, Charlotte, NC (US)

(72) Inventor: Madhusudhanan Krishnamoorthy, Chennai (IN)

(73) Assignee: BANK OF AMERICA CORPORATION, Charlotte, NC (US)

( * ) Notice: Subject to any disclaimer, the term of this patent is extended or adjusted under 35 U.S.C. 154(b) by 330 days.

(21) Appl. No.: 16/901,402

(22) Filed: Jun. 15, 2020

(65) Prior Publication Data
US 2021/0386313 A1  Dec. 16, 2021

(51) Int. Cl.
*A61B 5/398* (2021.01)
*G06N 20/00* (2019.01)
*A61B 3/113* (2006.01)
*G06N 3/08* (2006.01)
*G06F 3/01* (2006.01)

(52) U.S. Cl.
CPC .............. *A61B 5/398* (2021.01); *A61B 3/113* (2013.01); *G06F 3/013* (2013.01); *G06N 3/084* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 8,396,744 B2 | 3/2013 | Pradeep et al. | |
| 9,826,284 B2 | 11/2017 | Knight et al. | |
| 9,955,895 B2 | 5/2018 | Jin et al. | |
| 9,960,980 B2 | 5/2018 | Wilson | |
| 10,052,452 B2 | 8/2018 | Schoonover et al. | |
| 10,140,628 B2 | 11/2018 | Pradeep et al. | |
| 10,303,187 B1 * | 5/2019 | McNamara | G06F 7/00 |
| 10,360,467 B2 | 7/2019 | Yoo et al. | |
| 10,520,782 B2 | 12/2019 | Busch | |
| 2013/0235034 A1 | 9/2013 | Reitan | |
| 2013/0242077 A1 | 9/2013 | Lin et al. | |
| 2013/0249947 A1 | 9/2013 | Reitan | |
| 2014/0063061 A1 | 3/2014 | Reitan | |
| 2014/0164095 A1 | 6/2014 | Pradeep et al. | |
| 2014/0173555 A1 * | 6/2014 | Ng | G06F 16/9024 717/109 |
| 2015/0169431 A1 * | 6/2015 | Ivankovic | G06F 11/3676 717/124 |
| 2016/0235323 A1 | 8/2016 | Tadi et al. | |

(Continued)

*Primary Examiner* — Tapas Mazumder
(74) *Attorney, Agent, or Firm* — Moore & Van Allen PLLC; Nicholas C. Russell (57) ABSTRACT The present invention generally relates to the field of automated and flexible information extraction for review and analysis of computer code. In particular, the novel present invention provides a unique platform for analyzing, classifying, extracting, and processing information using multi-channel input from user devices and optical tracking sensors and employing the use of behavioral cloning network (BCN) technology. Embodiments of the inventions are configured to provide an end to end automated solution for extracting data from code review processes that can be used to automate and accelerate the code review and validation methods.

20 Claims, 6 Drawing Sheets (56) References Cited

U.S. PATENT DOCUMENTS

| | | |
|---|---|---|
| 2017/0000422 A1 | 1/2017 | Moturu et al. |
| 2017/0293356 A1 | 10/2017 | Khader et al. |
| 2018/0088323 A1 | 3/2018 | Bao et al. |
| 2018/0184002 A1 | 6/2018 | Thukral et al. |
| 2018/0368722 A1 | 12/2018 | Lunner et al. |
| 2019/0179328 A1 | 6/2019 | Movert et al. |
| 2019/0266516 A1 | 8/2019 | Dlabiyi |
| 2019/0384392 A1 | 12/2019 | Aimone et al. |
| 2020/0104685 A1 | 4/2020 | Hasenclever et al. |

* cited by examiner

SYSTEM USING EYE TRACKING DATA FOR ANALYSIS AND VALIDATION OF DATA

FIELD OF THE INVENTION

The present invention generally relates to the field of automated and flexible information extraction for review and analysis of computer code.

BACKGROUND

Current tools for code review are typically employed manually by human users. As such, the development of models which effectively achieve the same result is preferred, but difficult to accomplish in that the complex nature of human review may not be a linear exercise. It is advantageous to develop a model based on human code review in order to save time and expense while retaining accuracy and consistency. There is a need for a novel platform for analyzing, classifying, extracting, and processing information using multichannel input from user devices and optical tracking sensors. Embodiments of the inventions are configured to provide an end to end automated solution for extracting data from code review processes that can be used to automate and accelerate the code review and validation methods.

The previous discussion of the background to the invention is provided for illustrative purposes only and is not an acknowledgement or admission that any of the material referred to is or was part of the common general knowledge as at the priority date of the application.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

The present invention addresses the above needs by providing a system, methods, and computer program products for utilizing eye-tracking data for analysis and validation of code data in an automated review process. The invention may employ the use of electrooculography ("EOG") devices that track the eye movement of a human user, and use this data in coordination with code review demonstration data and prior knowledge data in order to train one or more machine learning models. Thus, the trained machine learning models may adapt to and mimic the human review process of reviewing and validating code using models trained on multichannel data indicative of the human review process, which, in some cases, is not fully reflected by the linear history of code revisions alone. The data provided by the EOG device during human demonstration allow the machine learning model to identify and analyze patterns of review and further optimize the review process by identifying logical relationships between code revision actions in light of a proper contextual basis of human focus. It is understood that while preferred embodiments discussed herein are generally related to the process of code review and validation, the multi-channel approach using EOG data could be extrapolated for any sort of human feedback tracking and emulation that employs the use of a behavioral cloning network.

Embodiments of the present invention comprise systems, methods, and computer program products that address these and/or other needs by providing an innovative and unique platform for analyzing, classifying, extracting, and processing information using multichannel input from user devices and optical tracking sensors. Embodiments of the inventions are configured to provide an end to end automated solution for extracting data from code review processes that can be used to automate and accelerate the code review and validation methods.

Typically the system comprises: at least one memory device with computer-readable program code stored thereon; at least one communication device; at least one processing device operatively coupled to the at least one memory device and the at least one communication device, wherein executing the computer-readable code is configured to cause the at least one processing device to: receive request data comprising code review data and code change data from a first data channel; generate eye movement data from a second data channel, wherein the eye movement data is generated using the electrooculography device; analyze the request data via a machine learning model to determine a relationship between code review data and code change data; determine contextual relationship between the eye movement data and analyzed request data; generate a modeling layer based on the analyzed request data and determined contextual relationship between the eye movement data and request data; apply the modeling layer to additional request data as a code review policy; back propagate the code review policy to compare results of the code review policy to labeled documentation generated by human review; and alter the modeling layer based on the results of the code review policy as compared to labeled documentation.

In some embodiments, the eye tracking data further comprises state of action data wherein the state of action data contains data on the sequential movement of a human eye in relation to a code snippet. In further embodiments, an attention weight is assigned to the eye tracking data based on state of action data.

In still other embodiments, a revised code policy of the altered modeling layer is continuously back propagated until a global minimum difference threshold is identified.

Additionally, the machine learning model further comprises a character embedding layer, a word embedding layer, and a context embedding layer for both the review data and code change data.

In some embodiments, the electrooculography device measures corneo-retinal standing potential that exists between the front and the back of a human eye.

Furthermore, the machine learning model further comprises an attention layer for determining relationship between code review data, code change data, and eye movement data in some embodiments.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Having thus described embodiments of the invention in general terms, reference will now be made to the accompanying drawings, wherein:

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

In some embodiments, an "entity" or "enterprise" as used herein may be any institution employing information technology resources and particularly technology infrastructure configured for large scale processing of electronic files, electronic technology event data and records, and performing/processing associated technology activities. In some instances, the entity's technology systems comprise multiple technology applications across multiple distributed technology platforms for large scale processing of technology activity files and electronic records. As such, the entity may be any institution, group, association, financial institution, establishment, company, union, authority or the like, employing information technology resources.

As described herein, a "user" is an individual associated with an entity. In some embodiments, a "user" may be an employee (e.g., an associate, a project manager, an IT specialist, a manager, an administrator, an internal operations analyst, or the like) of the entity or enterprises affiliated with the entity, capable of operating the systems described herein. In some embodiments, a "user" may be any individual, entity or system who has a relationship with the entity, such as a customer. In other embodiments, a user may be a system performing one or more tasks described herein.

In the instances where the entity is a financial institution, a user may be an individual or entity with one or more relationships affiliations or accounts with the entity (for example, a financial institution). In some embodiments, the user may be an entity or financial institution employee (e.g., an underwriter, a project manager, an IT specialist, a manager, an administrator, an internal operations analyst, bank teller or the like) capable of operating the system described herein. In some embodiments, a user may be any individual or entity who has a relationship with a customer of the entity. For purposes of this invention, the term "user" and "reviewer" may be used interchangeably.

As used herein, a "user interface" or "UI" may be an interface for user-machine interaction. In some embodiments the user interface comprises a graphical user interface. Typically, a graphical user interface (GUI) is a type of interface that allows users to interact with electronic devices such as graphical icons and visual indicators such as secondary notation, as opposed to using only text via the command line. That said, the graphical user interfaces are typically configured for audio, visual and/or textual communication. In some embodiments, the graphical user interface may include both graphical elements and text elements. The graphical user interface is configured to be presented on one or more display devices associated with user devices, entity systems, processing systems and the like. In some embodiments the user interface comprises one or more of an adaptive user interface, a graphical user interface, a kinetic user interface, a tangible user interface, and/or the like, in part or in its entirety.

Figure 1:
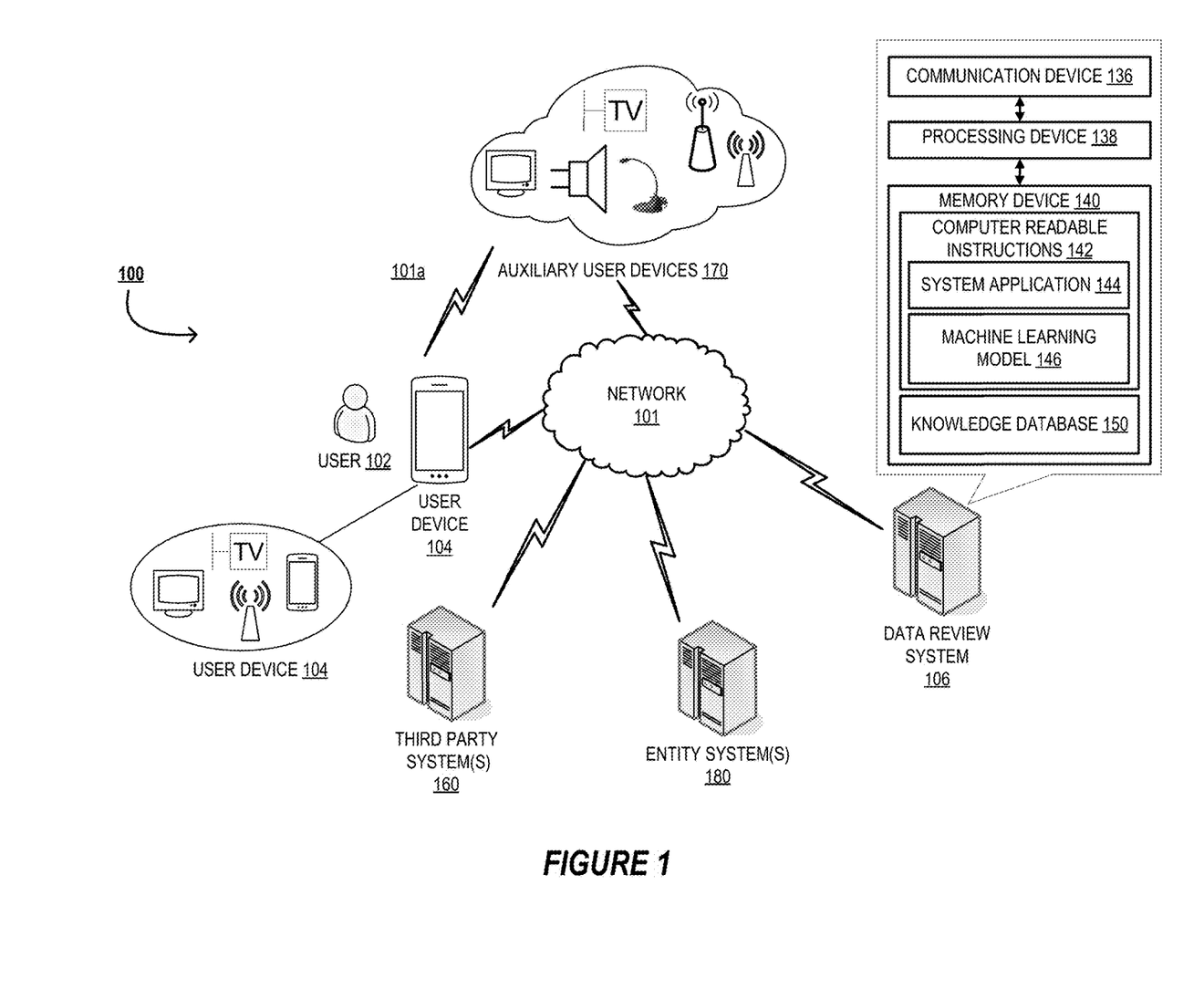
FIG. 1 depicts a system environment, in accordance with one embodiment of the present disclosure.

FIG. 1 depicts a platform environment 100 providing a system for analysis and validation of code data in an automated review process based on multi-channel inputs, in accordance with one embodiment of the present invention. As illustrated in FIG. 1, a data review system 106, configured for providing an intelligent, proactive and responsive application or system, at a user device 104, which facilitates execution of data review activities in an integrated manner. The data review system 106 is operatively coupled, via a network 101 to one or more user devices 104, auxiliary user devices 170, to entity systems 180, third party systems 160, and other external systems/third-party servers not illustrated herein. In this way, the data review system 106 can send information to and receive information from multiple user devices 104 and auxiliary user devices 170 to provide an integrated platform with multi-channel data review capabilities to a user 102, and particularly to the user device 104. At least a portion of the system for data review is typically configured to reside on the user device 104 (for example, at the user application 122), on the data review system 106 (for example, at the system application 144), and/or on other devices.

The network 101 may be a global area network (GAN), such as the Internet, a wide area network (WAN), a local area network (LAN), or any other type of network or combination of networks. The network 101 may provide for wireline, wireless, or a combination wireline and wireless communication between devices on the network 101. The network 101 is configured to establish an operative connection between otherwise incompatible devices, for example establishing a communication channel, automatically and in real time, between the one or more user devices 104 and one or more of the auxiliary user devices 170, as illustrated by communication channel 101a. Therefore, the system, via the network 101 may establish, operative connections between otherwise incompatible devices, for example by establishing a communication channel 101a between the one or more user devices 104 and the auxiliary user devices 170. In this regard, the network 101 (and particularly the communication channels 101a) may take the form of contactless interfaces, short range wireless transmission technology, such near-field communication (NFC) technology, Bluetooth® low energy (BLE) communication, audio frequency (AF)

waves, wireless personal area network, radio-frequency (RF) technology, and/or other suitable communication channels.

In some embodiments, the user 102 is an individual that wishes to conduct one or more activities with data review system 106 using the user device 104. In some embodiments, the user 102 may access the data review system 106, and/or the entity system 180 through a user interface comprising a webpage or a user application. Hereinafter, "user application" is used to refer to an application on the user device 104 of the user 102, a widget, a webpage accessed through a browser, and the like. As such, in some instances, the user device may have multiple user applications stored/installed on the user device 104 and the memory device 116 in particular. In some embodiments, the user application is a user application 122, also referred to as a "user application" 122 herein, provided by and stored on the user device 104 by the data review system 106. In some embodiments the user application 122 may refer to a third party application or a user application stored on a cloud used to access the data review system 106 and/or the auxiliary user device 170 through the network 101, communicate with or receive and interpret signals from auxiliary user devices 170, and the like. In some embodiments, the user application is stored on the memory device 140 of the data review system 106, and the user interface is presented on a display device of the user device 104, while in other embodiments, the user application is stored on the user device 104.

The user 102 may subsequently navigate through the interface or initiate one or more user activities or code review activities using a central user interface provided by the user application 122 of the user device 104. In some embodiments, the user 102 may be routed to a particular destination or entity location using the user device 104. In some embodiments the auxiliary user device 170 requests and/or receives additional information from the data review system 106/the resource entity system 160 and/or the user device 104 for authenticating the user and/or the user device, determining appropriate queues, executing information queries, and other functions.

FIG. 1 also illustrates the user device 104. The user device 104, herein referring to one or more user devices, wherein each device may generally comprise a communication device, a display device, a geo-positioning device, a processing device, and a memory device, as described further with regard to FIG. 2. Typically, the user device 104 is a computing system that allows a user 102 to interact with other systems to initiate or to complete code review and validation, or the like.

As further illustrated in FIG. 1, the data review system 106 generally comprises a communication device 136, at least one processing device 138, and a memory device 140. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 138 is operatively coupled to the communication device 136 and the memory device 140. The processing device 138 uses the communication device 136 to communicate with the network 101 and other devices on the network 101, such as, but not limited to the resource entity systems 160, auxiliary user devices 170 and/or the user device 104. As such, the communication device 136 generally comprises a modem, server, wireless transmitters or other devices for communicating with devices on the network 101. The memory device 140 typically comprises a non-transitory computer readable storage medium, comprising computer readable/executable instructions/code, such as the computer-readable instructions 142, as described below.

As further illustrated in FIG. 1, the data review system 106 comprises computer-readable instructions 142 or computer readable program code 142 stored in the memory device 140, which in one embodiment includes the computer-readable instructions 142 of a system application 144 (also referred to as a "system application" 144). The computer readable instructions 142, when executed by the processing device 138 are configured to cause the system 106/processing device 138 to perform one or more steps described in this disclosure to cause out systems/devices (such as the user device 104, the user application 122, and the like) to perform one or more steps described herein. In some embodiments, the memory device 140 includes a data storage for storing data related to code review and validation, but not limited to data created and/or used by the system application 144. Data review system 106 also includes machine learning model 146. In some embodiments, the machine learning model 146 is used to analyze received data in order to identify complex patterns and intelligently improve the efficiency and capability of the data review system 106 to analyze received multi-channel data and identify patterns usable to formulate model policies. In some embodiments, the machine learning model 146 may include supervised learning techniques, unsupervised learning techniques, or a combination of multiple machine learning models that combine supervised and unsupervised learning techniques. In some embodiments, the machine learning model may include an adversarial neural network that uses a process of encoding and decoding in order to adversarial train one or more machine learning models to identify relevant patterns in received data received from one or more channels of communication such as the multi-channel data received from the user devices 104 and auxiliary user devices 170 (e.g., code review data from user device 104, contextual data from one or more entity systems, optical sensor tracking data from an EOG device, or the like).

FIG. 1 further illustrates one or more auxiliary user devices 170, in communication with the network 101. The auxiliary user devices 170 may comprise peripheral devices such as sensors, input devices, wearable devices, or the like. In the embodiment illustrated in FIG. 1, and described throughout much of this specification, a "system" configured for performing one or more steps described herein refers to the user application 122, that may perform one or more user activities either alone or in conjunction with the data review system 106, and specifically, the system application 144, one or more auxiliary user device 170, and the like in order to provide multi-channel input solutions described herein.

The user application 122 is configured to support an interface wherein the user 102 may interact with and utilize the data review system and its capabilities. In this regard, in some embodiments, the central user interface is presented on one or more user devices via the user application 122 or another user application 122. The central user interface associated with the user application 122 may be presented on the display device 112 of the user device 104 via an application programming interface (API) protocol that allows data to be submitted to and requested form the data review system 106. Additionally, the user application 122 may be configured to provide diagnostic and administrative capabilities to the user 102 such that the user may administer the training and management of the machine learning model 146 of the data review system 106.

Also pictured in FIG. 1 are one or more third party systems 160, which are operatively connected to the data review system 106 via network 101 in order to transmit data to and receive data from the data review system 106. For instance, the capabilities of the data review system 106 may be leveraged in some embodiments by third party systems in order to streamline, audit, or expedite code review processes. In other embodiments, the third party systems 160 may provide contextual data from human users or data review policies that the data review system 106 can utilize in the training process of the machine learning models. In some embodiments, multi-channel data processing capabilities may be provided as a service by the data review system 106 to the entity systems 180, third party systems 160, or additional systems and servers not pictured, through the use of an application programming interface ("API") designed to simplify the communication protocol for client-side requests for data or services from the data review system 106. In this way, the capabilities offered by the present invention may be leveraged by multiple parties other than the those controlling the data review system 106 or entity systems 180.

Though not shown in detail, the system further includes one or more entity systems 180 which is connected to the user device 104 and the data review system 106 and which may be associated with one or more entities, institutions, third party systems 160, or the like. In this way, while only one entity system 180 is illustrated in FIG. 1, it is understood that multiple networked systems may make up the system environment 100. The entity system 180 generally comprises a communication device, a processing device, and a memory device. The entity system 180 comprises computer-readable instructions stored in the memory device, which in one embodiment includes the computer-readable instructions of an entity application. The entity system 180 may communicate with the user device 104 and the data review system 106 to provide access to user accounts stored and maintained on the entity system 180. In some embodiments, the entity system 180 may communicate with the data review system 106 during an interaction with a user 102 in real-time, wherein user interactions may be monitored and processed by the data review system 106 in order to analyze interactions with the user 102 and reconfigure the machine learning model in response to changes in a received or monitored data stream. In one embodiment, the system is configured to receive data for decisioning, wherein the received data is processed and analyzed by the machine learning model to determine a conclusion.

Figure 2:
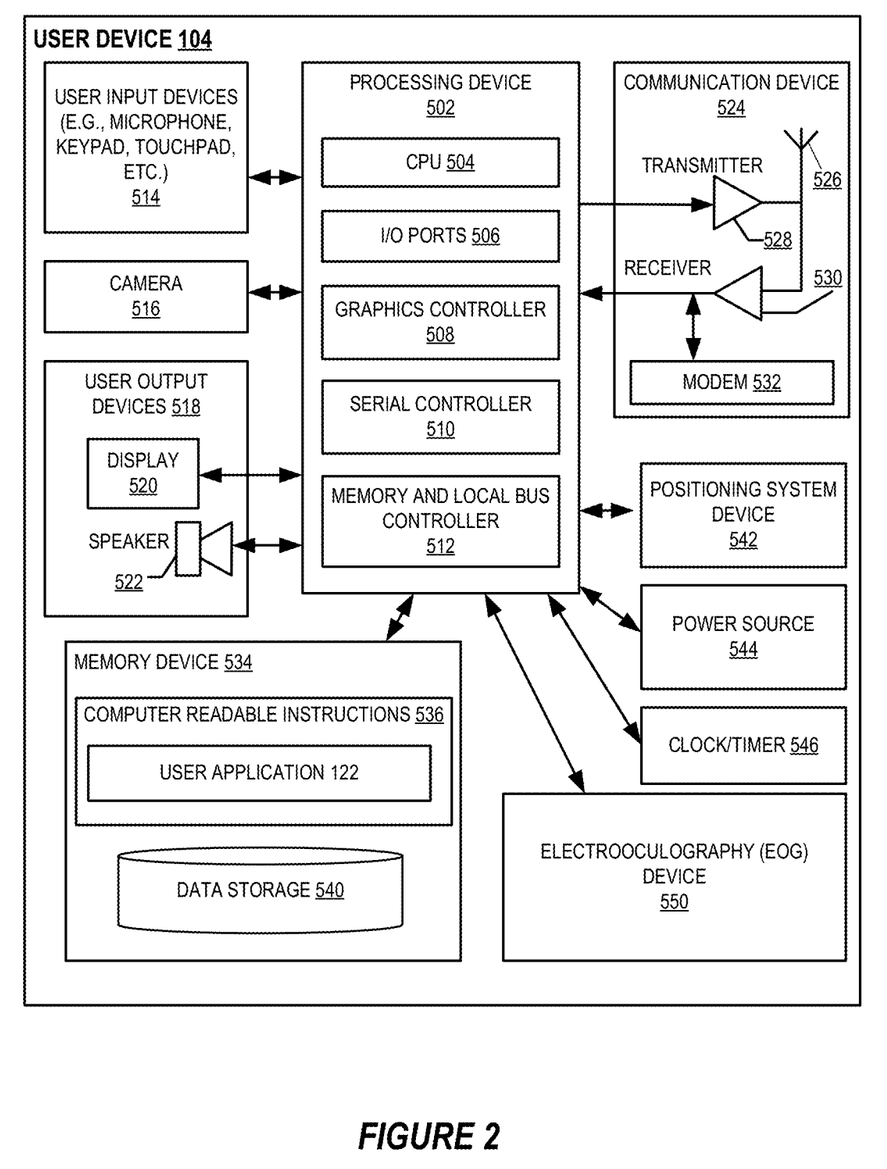
FIG. 2 provides a block diagram of the user device 104, in accordance with one embodiment of the present disclosure.

FIG. 2 provides a block diagram of the user device 104, in accordance with one embodiment of the invention. The user device 104 may generally include a processing device or processor 502 communicably coupled to devices such as, a memory device 534, user output devices 518 (for example, a user display device 520, or a speaker 522), user input devices 514 (such as a microphone, keypad, touchpad, touch screen, and the like), a communication device or network interface device 524, a power source 544, a clock or other timer 546, a visual capture device such as a camera 516, a positioning system device 542, such as a geo-positioning system device like a GPS device, an accelerometer, and the like. The processing device 502 may further include a central processing unit 504, input/output (I/O) port controllers 506, a graphics controller or graphics processing device (GPU) 208, a serial bus controller 510 and a memory and local bus controller 512.

The processing device 502 may include functionality to operate one or more software programs or applications, which may be stored in the memory device 534. For example, the processing device 502 may be capable of operating applications such as the user application 122. The user application 122 may then allow the user device 104 to transmit and receive data and instructions from the other devices and systems of the environment 100. The user device 104 comprises computer-readable instructions 536 and data storage 540 stored in the memory device 534, which in one embodiment includes the computer-readable instructions 536 of a user application 122. In some embodiments, the user application 122 allows a user 102 to access and/or interact with other systems such as the entity system 180, third party system 160, or data review system 106. In one embodiment, the user 102 is a maintaining entity of a data review system 106, wherein the user application enables the user 102 to define policies and reconfigure the data review system 106 or its components. In one embodiment, the user 102 is a customer of a financial entity and the user application 122 is an online application or API enabled application providing access to the entity system 180 wherein the user may interact with a user account via a user interface of the user application 122, wherein the user interactions may be provided in a data stream as an input via multiple channels. In some embodiments, the user 102 may a customer of third party system 160 that requires the use or capabilities of the data review system 106 for authorization or verification purposes.

The processing device 502 may be configured to use the communication device 524 to communicate with one or more other devices on a network 101 such as, but not limited to the entity system 180 and the data review system 106. In this regard, the communication device 524 may include an antenna 526 operatively coupled to a transmitter 528 and a receiver 530 (together a "transceiver"), modem 532. The processing device 502 may be configured to provide signals to and receive signals from the transmitter 528 and receiver 530, respectively. The signals may include signaling information in accordance with the air interface standard of the applicable BLE standard, cellular system of the wireless telephone network and the like, that may be part of the network 101. In this regard, the user device 104 may be configured to operate with one or more air interface standards, communication protocols, modulation types, and access types. By way of illustration, the user device 104 may be configured to operate in accordance with any of a number of first, second, third, and/or fourth-generation communication protocols or the like. For example, the user device 104 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, and/or the like. The user device 104 may also be configured to operate in accordance with non-cellular communication mechanisms, such as via a wireless local area network (WLAN) or other communication/data networks. The user device 104 may also be configured to operate in accordance, audio frequency, ultrasound frequency, or other communication/data networks.

The user device 104 may also include a memory buffer, cache memory or temporary memory device operatively coupled to the processing device 502. Typically, one or more applications, are loaded into the temporarily memory during use. As used herein, memory may include any computer readable medium configured to store data, code, or other information. The memory device 534 may include volatile memory, such as volatile Random Access Memory (RAM) including a cache area for the temporary storage of data. The memory device 534 may also include non-volatile memory, which can be embedded and/or may be removable. The non-volatile memory may additionally or alternatively include an electrically erasable programmable read-only memory (EEPROM), flash memory or the like.

The user device 104 may also include an electrooculography (EOG) device 550 used to provide data for a technique for measuring the corneo-retinal standing potential that exists between the front and the back of the human eye. The resulting signal is called an electrooculogram which may be transmitted as optical tracking data from the user device 104 to the data review system 106. A primary application for the use of this optical tracking data as described here is the process of recording eye movements, which can then be used contextually in as data in a behavioral cloning machine learning model. It is understood that while FIG. 2 shows the EOG device 550 as a part of the user device 104, the EOG device may exist separately as a form of auxiliary user device 170 in some embodiments.

Figure 3:
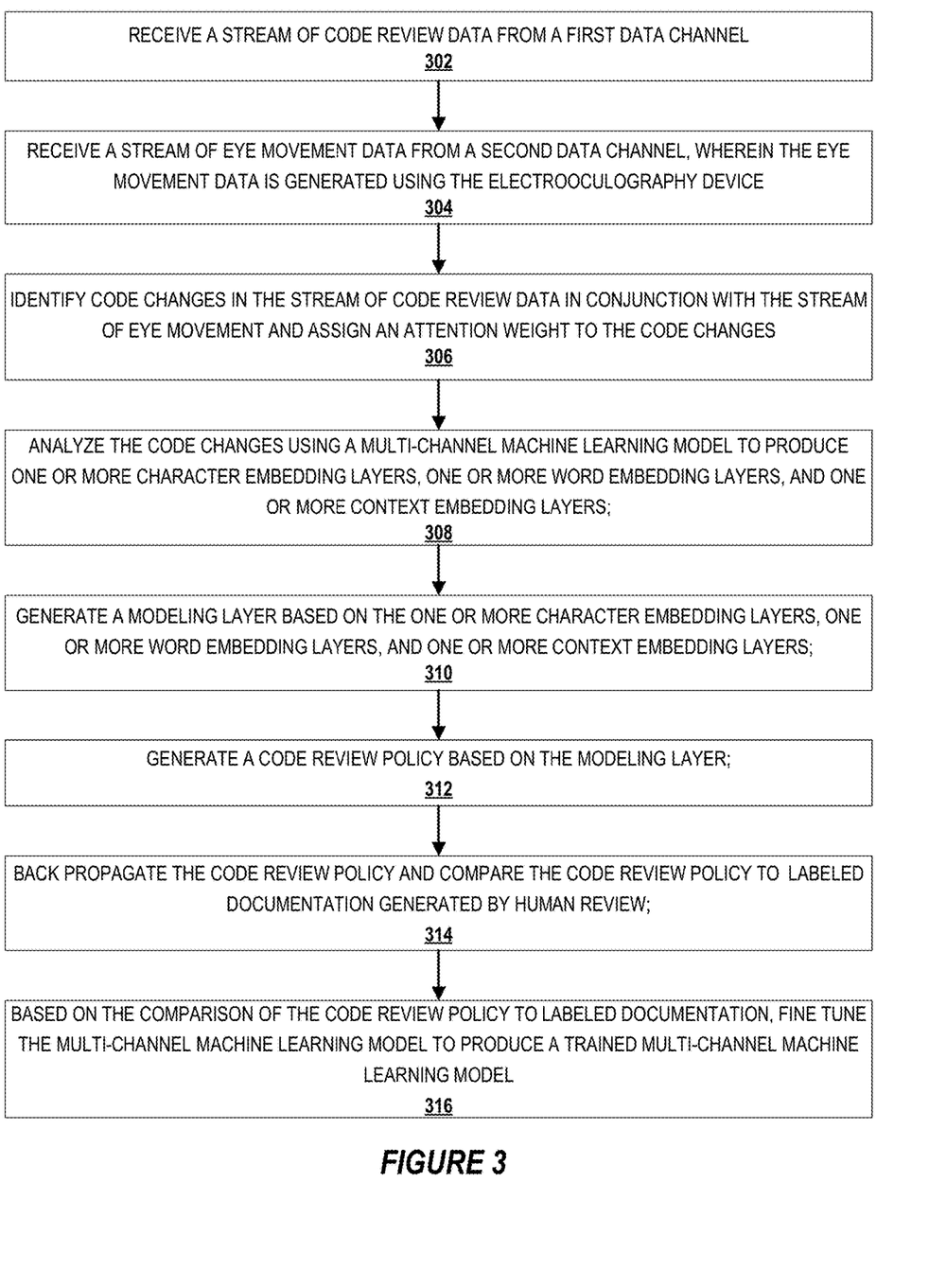
FIG. 3 depicts a process flow diagram of multi-channel machine learning model training using optical eye tracking data, in accordance with one embodiment of the present disclosure.

FIG. 3 depicts a process flow diagram of multi-channel machine learning model training using eye tracking data, in accordance with one embodiment of the present invention. As shown, the process begins at blow 302, wherein the system receives a stream of code review data from a first data channel. In some embodiments, this may be the data channel associated with code review, wherein a human user reviews, revises and validates code via a user device 104. The system may receive a continuous stream of data from the user device 104 indicating the changes in code throughout the code analysis and review process. In other embodiments, the code data may be stored on the data review system 106, wherein the user transmits a stream of instructions for code revision to the data review system 106. In other embodiments, the code for review may exists on another entity system, and the user may similarly use a user device 104 to transmit instructions for code revision and review over the network 101 to the entity system and the data review system may also receive a copy of this data stream.

Next, as shown in block 304, the system also receives a stream of eye movement data, or eye movement data, from a second data channel, wherein the eye movement data is generated using the electrooculography device. In some embodiments, the electrooculography device may be a component of the user device 104, wherein in other embodiments, the electrooculography device may be a standalone device such as auxiliary user device 170. The electrooculography device may be worn by the user and data may be transmitted over network 101 to the data review system 106.

As shown in block 306, the process proceeds to identifying code changes in the stream of code review data in conjunction with the stream of eye movement and assign an attention weight to the code changes. In some embodiments, the data streamed from the user device or entity system via the first data stream may not require identification of code changes, as it may simply be data representing instructions for code changes. Based on the eye movement data, and state of action data later described with regard to FIG. 6, the system may determine where the user is looking on the screen of a user device, how much time the user spends focused on that particular location, and the sequential movement of the human eye across the code. By comparing this data with the code review data, and corresponding code changes, the system may correlate the user's attention with the code changes and may assign an attention weight to a particular portion of the code depending on a number of variables, including the amount in which the code is changed, the time the user spent focused on that code portion, or the like. A code portion may be determined as a character, a word, a variable, a term, a line of code, or the like, depending on the code changes or revisions identified in the code, or depending on the contextual syntax of the particular code portion. As shown in block 308, the system uses this data to analyze the code changes using a multi-channel machine learning model to produce one or more character embedding layers, one or more word embedding layers, and one or more context embedding layers in order to store and analyze this information.

Next, as shown in block 310, the system may generate a modeling layer based on the one or more character embedding layers, one or more word embedding layers, and one or more context embedding layers, and use this data to generate a code review policy based on the modeling layer as shown in block 312. The system may then back-propagate the code review policy and compare the code review policy to labeled documentation generated by human review, as shown in block 314. Based on the comparison of the code review policy to labeled documentation, the system may fine tune the multi-channel machine learning model to produce a trained multi-channel machine learning model code review policy, as shown in block 316.

Figure 4:
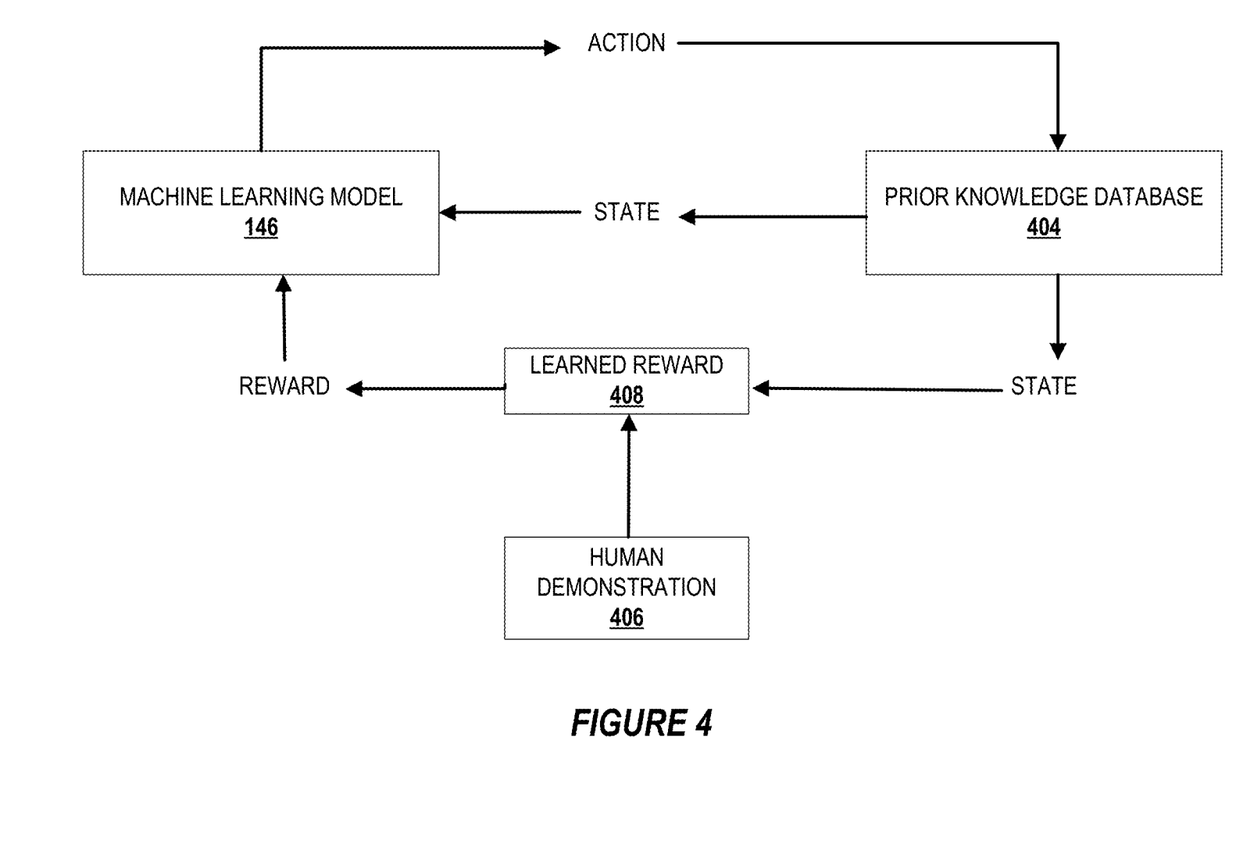
FIG. 4 depicts a high level process flow for a behavioral cloning network, in accordance with embodiments of the present invention.

FIG. 4 depicts a high level process flow for a behavioral cloning network, in accordance with embodiments of the present invention. In conventional systems, code review by experts along with quality assurance (QA), and automation of screen shots comparison are two critical, albeit time consuming, processes as they act as the last line of defense against potentially harmful code errors before moving code into a production environment. These processes essentially provide a qualitative guarantee which could not be obtained by technical code review policies, or even hand labeled data into a deep learning sophisticated architecture. As such, the key to an improved intelligent system for automating the processes of (1) code validation and (2) code QA are needed. Seeing as there needs to be a solution which gradually learns along with a team of coding experts and also possesses the ability to automate code QA, there is a need to loop-in human input ("human-in-the-loop training") to continuously monitor and optimize the model based on this human input data. The present invention's solution to this need partly involves the use of a behavioral cloning network (BCN), as depicted here in FIG. 4.

The use of BCN is an emerging paradigm where autonomous agents learn from human demonstration to perform complex tasks. BCN views a human demonstration as an exemplar of prior knowledge in its working system and leverages a set of human demonstrations to work on tasks whose reward functions may be difficult to define a priori. The paradigm can be successfully applied to code review methods for reinforcement leaning in the present invention. As shown in FIG. 4, the process generally includes a continuous feedback loop of training for the machine learning model 146 wherein the model receives data from human demonstration 406 and incorporates data from prior knowledge database 404 in order to produce learned reward(s) 408. The machine learning model 146 produces actions which are used to continuously update the prior knowledge database 404 (e.g., such as knowledge database 150). The model then relies on data from the prior knowledge database 404 to intelligently analyze the state of incoming data feeds. As shown, learned reward(s) 408 include a combination of state knowledge and data from human demonstration 406 in order for the AI/machine learning model 146 to base its reward and training accuracy on such human demonstrations and in turn continue to update the prior knowledge database until a statistically meaningful convergence confidence is achieved.

Figure 5:
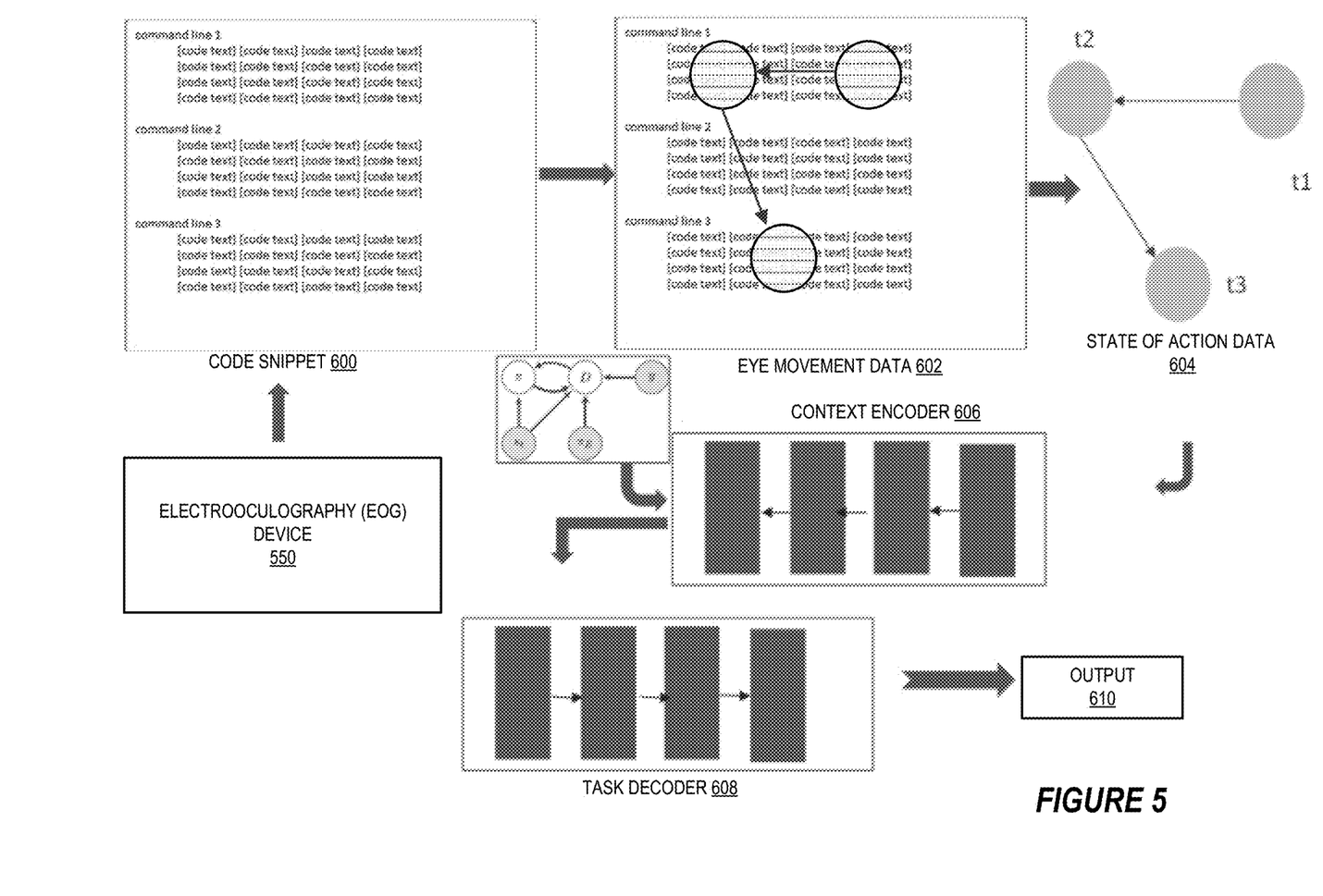
FIG. 5 depicts a process flow diagram of multichannel input and analysis, in accordance with embodiments of the present invention.

FIG. 5 depicts a process flow diagram of multichannel input and analysis, in accordance with embodiments of the present invention. As shown in FIG. 5, the system may receive data from the EOG device 550 which may be combined with code snippet 600 in order to actively analyze the location of eye movement data 602 across the code snippet 600. This graphical depiction in FIG. 5 is a conceptualized visual representation of how the data is combined and processed by the data review system during machine learning model 146 training. As shown, state of action data 604 not only includes the location of eye movement data 602, as shown by the highlighted elliptical areas on eye movement data 602, but also comprises the sequential movement between locations as shown by the arrows from t1 to t2 to t3.

Figure 6:
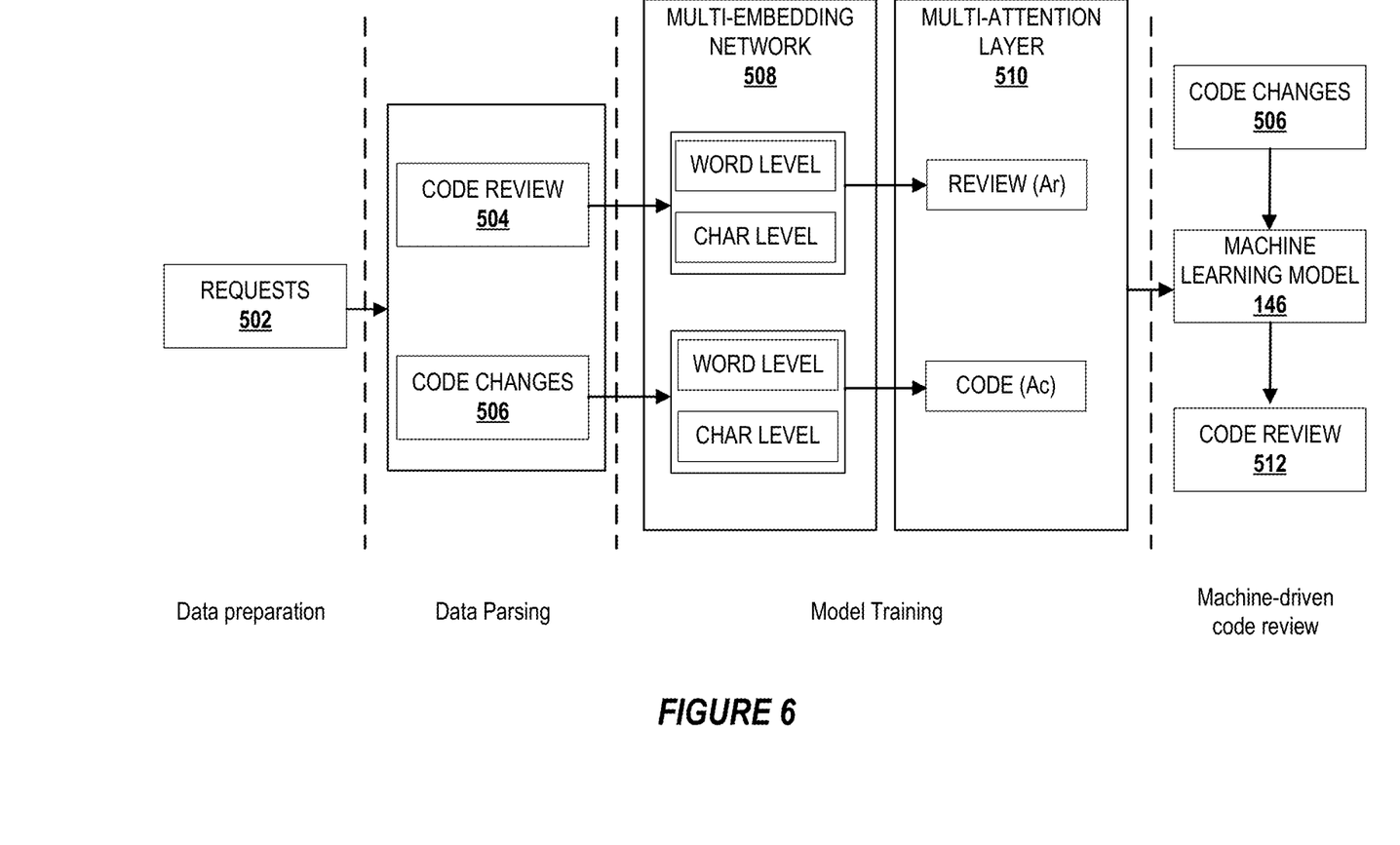
FIG. 6 depicts a high level process flow for a BCN driven training of the machine learning model, in accordance with embodiments of the present invention.

State of action data is next sent to a context encoder 606, and a task decoder 608, which are used by the machine learning model 146 in order to infer tasks based on state of action data 604, eye movement data 602, and contextual data received from requests as described in FIG. 6, such as code review and code changes. In this way, the system uses multiple context encoding layers and task decoder layers in order to infer relationships between variables in the multi-channel data. The output 610 may be stored at the machine learning model to inform the code review policy, which again is back propagated for fine tuning based on identified discrepancies between human code review and the output of the machine learning model until the global minimum difference threshold is reached, resulting in a trained machine learning model 146 that may automate the code review process using informed analysis of various human input and perceived changes in received code.

FIG. 6 depicts a high level process flow for a BCN driven training of the machine learning model, in accordance with embodiments of the present invention. The process flow begins at requests 502 in a data preparation stage. Typically during human review, users may submit code changes to a reviewing body so that review can be completed and a determination can be made as to whether the changes should be merged with the overall project. The user authoring the request will request review for submitted code changes from the other contributors to the project. The main contributors are usually experienced expert developers with deep involvement in the overall project. In this instance, these requests 502 can be used to train the machine learning model 146 through BCN driven training.

The requests 502 are fed to the data parsing stage which includes code review 504 and code changes 506. Code review 504 generally comprises qualitative suggestions or notation provided in conjunction with code changes 506, which comprise changes in the code itself. For instance, a user reviewing code may suggest that a particular command be replaced with a substitute command that may lead to reduction of error in execution of the code (i.e., suggest a code change 506). Along with suggesting the code change 506, the reviewing user may include a helpful note such as "consider replacing this line of code," in the form of a code review 504.

Data from the data parsing stage is then fed to the model training layer. The model training layer includes a multi-embedding network 508, wherein the code review 504 and code change 506 are analyzed at a word level and character level. The multi-embedding network 508 including coding logic for character embedding layers, word embedding layers, as well as context embedding layers (e.g., a broader contextual meaning for several lines of code wherein name of function or scope may vary). Data from the multi-embedding network 508 is fed to a multi-attention layer 510, which is a layer that uses state of actions to determine an indication of which lines of code being activated most based on human observation data. In this way, the model receives data regarding code input, but also human tracking input, thereby comprising a binary input model. However, the multi-attention layer 510 itself does not simply involve a binary process, but rather may assign a variation of attention weights to state of action data, as described in FIG. 6. The model training stage outputs a code review policy (e.g., as represented by "review Ar" and "code Ac") which is sent to the machine-driven code review stage to be stored for the machine learning model 146. As shown, the machine learning model 146 may continue to receive raw code changes 506 and output its own code review 512, which may then be back propagated for fine tuning based on identified differences between code review 506 and code review 512. Once a global minimum difference threshold is reached between machine learning model 146 review and human review, training may be stopped.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, micro-code, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

It will be further understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A system for analysis and validation of code data, the system comprising:
   at least one memory device with computer-readable program code stored thereon;
   at least one communication device;
   at least one electrooculography device;
   at least one processing device operatively coupled to the at least one memory device and the at least one communication device, wherein executing the computer-readable code is configured to cause the at least one processing device to:
      receive request data comprising code review data and code change data from a first data channel;
      generate eye movement data from a second data channel, wherein the eye movement data is generated using an electrooculography device;
      analyze the request data via a machine learning model to determine a relationship between code review data and code change data;
      determine contextual relationship between the eye movement data and analyzed request data;
      generate a modeling layer based on the analyzed request data and determined contextual relationship between the eye movement data and request data;
      apply the modeling layer to additional request data as a code review policy;
      back propagate the code review policy to compare results of the code review policy to labeled documentation generated by human review; and
      alter the modeling layer based on the results of the code review policy as compared to labeled documentation.

2. The system of claim 1, wherein the eye movement data further comprises state of action data wherein the state of action data contains data on sequential movements of a human eye in relation to a code snippet.

3. The system of claim 1, wherein an attention weight is assigned to the eye movement data based on state of action data.

4. The system of claim 1, wherein a revised code policy of the altered modeling layer is continuously back propagated until a global minimum difference threshold is identified.

5. The system of claim 1, wherein the machine learning model further comprises an attention layer for determining relationship between code review data, code change data, and eye movement data.

6. The system of claim 1, wherein the machine learning model further comprises a character embedding layer, a word embedding layer, and a context embedding layer for both the review data and code change data.

7. The system of claim 1, wherein the electrooculography device measures corneo-retinal standing potential that exists between an outward portion and an inward portion of a human eye.

8. A computer program product for analysis and validation of code data, wherein the computer program product is configured to provide a multi-channel resource platform, the computer program product comprising a non-transitory computer-readable storage medium having computer-executable instructions to:

receive request data comprising code review data and code change data from a first data channel;

generate eye movement data from a second data channel, wherein the eye movement data is generated using an electrooculography device;

analyze the request data via a machine learning model to determine a relationship between code review data and code change data;

determine contextual relationship between the eye movement data and analyzed request data;

generate a modeling layer based on the analyzed request data and determined contextual relationship between the eye movement data and request data;

apply the modeling layer to additional request data as a code review policy;

back propagate the code review policy to compare results of the code review policy to labeled documentation generated by human review; and alter the modeling layer based on the results of the code review policy as compared to labeled documentation.

9. The computer program product of claim 8, wherein the eye movement data further comprises state of action data wherein the state of action data contains data on sequential movements of a human eye in relation to a code snippet.

10. The computer program product of claim 8, wherein an attention weight is assigned to the eye movement data based on state of action data.

11. The computer program product of claim 8, wherein a revised code policy of the altered modeling layer is continuously back propagated until a global minimum difference threshold is identified.

12. The computer program product of claim 8, wherein the machine learning model further comprises an attention layer for determining relationship between code review data, code change data, and eye movement data.

13. The computer program product of claim 8, wherein the machine learning model further comprises a character embedding layer, a word embedding layer, and a context embedding layer for both the review data and code change data.

14. The computer program product of claim 8, wherein the electrooculography device measures corneo-retinal standing potential that exists between an outward portion and an inward portion of a human eye.

15. A computer automated and intelligent analysis of information, the computer implemented method comprising:

providing a computing system comprising a computer processing device and a non-transitory computer readable medium, where the non-transitory computer readable medium comprises configured computer program instruction code, such that when said instruction code is operated by said computer processing device, said computer processing device performs the following operations:

receiving request data comprising code review data and code change data from a first data channel;

generating eye movement data from a second data channel, wherein the eye movement data is generated using an electrooculography device;

analyzing the request data via a machine learning model to determine a relationship between code review data and code change data;

determining contextual relationship between the eye movement data and analyzed request data;

generating a modeling layer based on the analyzed request data and determined contextual relationship between the eye movement data and request data;

applying the modeling layer to additional request data as a code review policy;

back propagating the code review policy to compare results of the code review policy to labeled documentation generated by human review; and altering the modeling layer based on the results of the code review policy as compared to labeled documentation.

16. The computer implemented method of claim 15, wherein the eye movement data further comprises state of action data wherein the state of action data contains data on sequential movements of a human eye in relation to a code snippet.

17. The computer implemented method of claim 15, wherein an attention weight is assigned to the eye movement data based on state of action data.

18. The computer implemented method of claim 15, wherein a revised code policy of the altered modeling layer is continuously back propagated until a global minimum difference threshold is identified.

19. The computer implemented method of claim 15, wherein the machine learning model further comprises an attention layer for determining relationship between code review data, code change data, and eye movement data.

20. The computer implemented method of claim 15, wherein the electrooculography device measures corneo-retinal standing potential that exists between an outward portion and an inward portion of a human eye.

* * * * *